United States Patent
Henein

(10) Patent No.: US 11,043,299 B2
(45) Date of Patent: Jun. 22, 2021

(54) REDUCING NETWORK SECURITY RISKS IN A MEDICAL CARE NETWORK

(71) Applicant: BlackBerry Limited, Waterloo (CA)

(72) Inventor: Nader Saad Henein, Dubai (AE)

(73) Assignee: BlackBerry Limited, Waterloo (CA)

( * ) Notice: Subject to any disclaimer, the term of this patent is extended or adjusted under 35 U.S.C. 154(b) by 254 days.

(21) Appl. No.: 15/799,913

(22) Filed: Oct. 31, 2017

(65) Prior Publication Data
US 2019/0130075 A1  May 2, 2019

(51) Int. Cl.
| | |
|---|---|
| *G16H 40/40* | (2018.01) |
| *G06F 21/62* | (2013.01) |
| *G06F 19/00* | (2018.01) |
| *H04W 12/00* | (2021.01) |
| *G16H 40/20* | (2018.01) |
| *G06F 21/57* | (2013.01) |
| *G16H 10/60* | (2018.01) |

(52) U.S. Cl.
CPC ........... *G16H 40/40* (2018.01); *G06F 19/321* (2013.01); *G06F 21/577* (2013.01); *G06F 21/6245* (2013.01); *G16H 10/60* (2018.01); *G16H 40/20* (2018.01); *H04W 12/00* (2013.01)

(58) Field of Classification Search
None
See application file for complete search history.

(56) References Cited

U.S. PATENT DOCUMENTS

| | | | | |
|---|---|---|---|---|
| 2012/0179012 A1* | 7/2012 | Saffarian | .............. | A61B 5/0022 600/324 |
| 2013/0160082 A1* | 6/2013 | Miller | ..................... | H04L 63/08 726/3 |
| 2013/0247194 A1* | 9/2013 | Jha | ......................... | H04W 12/12 726/23 |
| 2014/0379368 A1* | 12/2014 | Kim | ...................... | G06Q 50/22 705/2 |

(Continued)

OTHER PUBLICATIONS

Grenert, "HIPAA-compliant configuration guidelines for Information Security in a Medical Center environment," SANS Institute InfoSec Reading Room; Aug. 4-9, 2002; 18 pages; <https://www.sans.org/reading-room/whitepapers/hipaa/hipaa-compliant-configuration-guidelinesinformation-security-medical-center-environment-891>.

(Continued)

*Primary Examiner* — Eleni A Shiferaw
*Assistant Examiner* — Bassam A Noaman
(74) *Attorney, Agent, or Firm* — Fish & Richardson P.C.

(57) ABSTRACT

Systems, methods, and software can be used to reduce network security risks in a medical care network. In some aspects, a method includes detecting, at a medical equipment monitor located in a network, an electronic device that is connected to the network; determining, by the medical equipment monitor, that the electronic device comprises a medical equipment; associating, by the medical equipment monitor, a security profile with the medical equipment, wherein the security profile includes one or more security parameters; detecting, by the medical equipment monitor, a conflict between a data transmission activity from the medical equipment and at least one security parameter in the security profile; and in response to detecting the conflict, transmitting, from the medical equipment monitor, a notification of the conflict to a medical equipment controller.

9 Claims, 4 Drawing Sheets

(56) References Cited

U.S. PATENT DOCUMENTS

| | | | |
|---|---|---|---|
| 2015/0382198 A1* | 12/2015 | Kashef | H04L 63/08 726/5 |
| 2018/0115574 A1* | 4/2018 | Ridley | G06F 21/572 |
| 2018/0122518 A1* | 5/2018 | Choudhary | G06F 19/3418 |
| 2019/0228863 A1* | 7/2019 | Dharwad | G16H 20/17 |

OTHER PUBLICATIONS

Rouse, "ICMP (Internet Control Message Protocol) Definition," Search Networking; TechTarget; 5 pages; <http://searchnetworking.techtarget.com/definition/ICMP>.

* cited by examiner

REDUCING NETWORK SECURITY RISKS IN A MEDICAL CARE NETWORK

TECHNICAL FIELD

The present disclosure relates to reducing network security risks in a medical care network.

BACKGROUND

In some implementations, a medical care network can include many medical devices that are connected via Internet Protocol (IP) communications to facilitate healthcare tasks. For example, these connectable medical devices can include large imaging chambers that can read patient data from Hospital Information Systems (HIS), deposit scan results, and signal an update to the residing physician. These connectable medical devices can also include small wearable medical devices that can transmit patient vitals to physicians, either directly or via a smartphone.

DESCRIPTION OF DRAWINGS

Like reference numbers and designations in the various drawings indicate like elements.

DETAILED DESCRIPTION

Connectable medical devices provide connectivity for dissemination of medical information, but also introduce security risks to patients and the privacy of patient data. For example, a malicious medical device can read a patient's private files, act as an access point for intruders to a hospital's network, or compromise other medical devices and put patients' health at risk. Examples of comprising other medical devices can include: administering incorrect dosages of medicine, providing false indication of medical emergency or alarms, and concealing bona fide emergencies from medical staff.

Unlike devices in a traditional communications network, such as a corporate network, providing security in a medical care network provides a different challenge. For example, a suspect medical device may not simply be blocked from connecting because a false positive may have a negative result on a patient. There are a wide variety of medical devices, including embedded systems, which make it difficult to manage. The manufacturers and regulators of the medical devices may not be as familiar with network technology and security implementations as their counterparts for general purpose computing devices. The operator of the medical care network, e.g., the hospital, may not have the technical expertise in managing security risks in the network.

In some implementations, the network security of a medical care network can be improved by actively monitoring the data transmission activities of the medical devices that are connected to the medical care network. One or more medical equipment monitors (MEMs) can be installed in the medical care network. The MEMs can detect devices that are connected to the medical care network, identify the medical devices to be monitored among these connected devices, associate security profiles with the medical devices, monitor the data transmission activities of the medical devices, and transmit a notification to a medical equipment controller (MEC) if a data transmission activity is determined to be in conflict with configurations set in the security profile. The MEC can provide an interface to the administrator to provision the security profiles, adjust the associations of security profiles, and receive the notifications. FIGS. 1-5 and associated descriptions provide additional details of these implementations.

Figure 1:
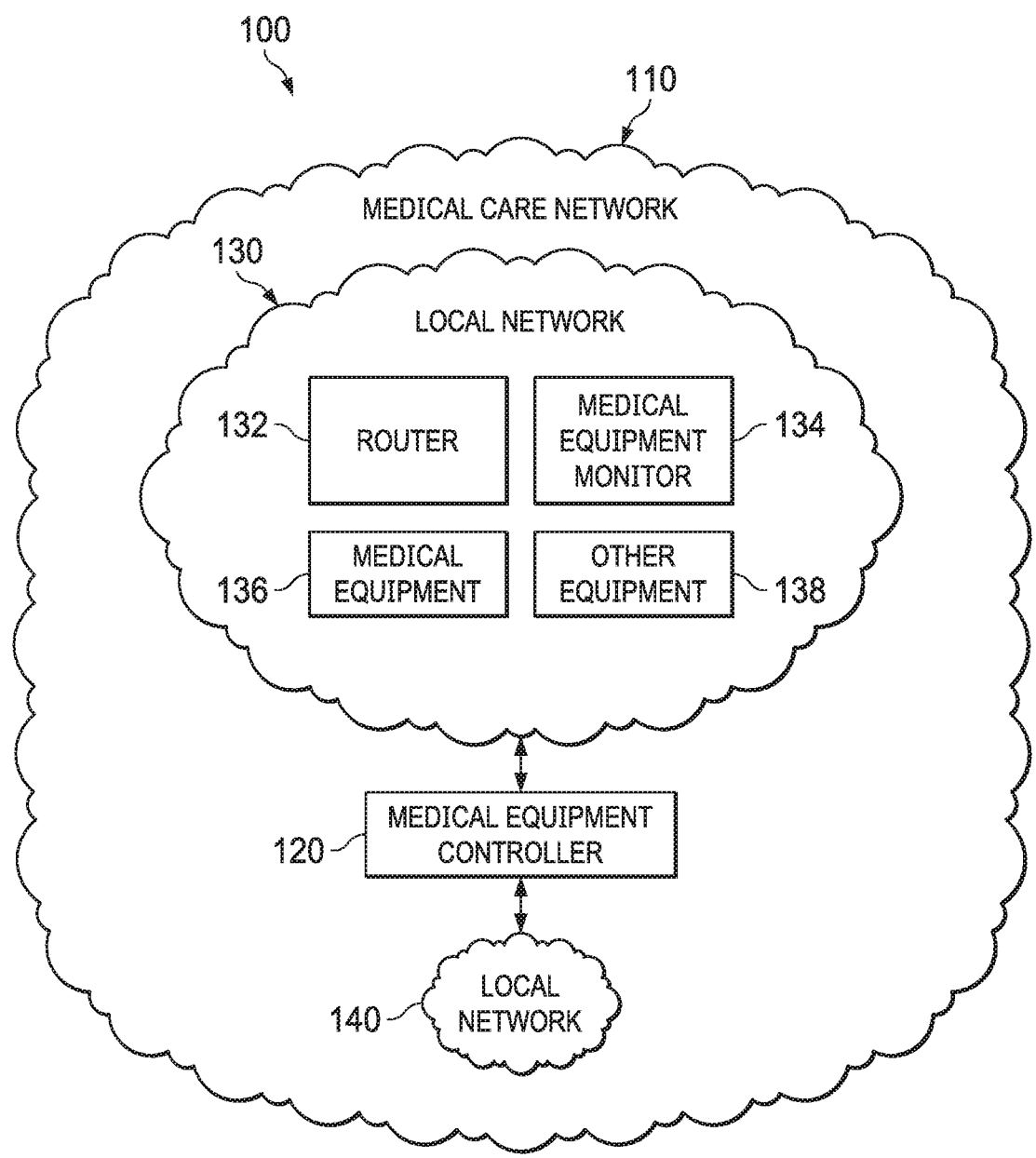
FIG. 1 is a schematic diagram showing an example communication system that reduces network security risks in a medical care network, according to an implementation.

FIG. 1 is a schematic diagram showing an example communication system 100 that reduces network security risks in a medical care network, according to an implementation. At a high level, the example communication system 100 includes a medical care network 110. The medical care network 110 includes local networks 130 and 140 that are communicatively coupled with an MEC 120.

The medical care network 110 represents a communication network that provides connectivity to electronic devices for health care applications. The medical care network 110 can include a wireless network, a wireline network, the Internet, or a combination thereof. For example, the medical care network 110 can include one or a plurality of radio access networks (RANs), core networks (CNs), and the Internet. The RANs may comprise one or more wireless radio access technologies. The medical care network 110 can also include coaxial cables, fiber optical cables, or other wireline access equipment. In some cases, the medical care network 110 can be owned, operated, or both owned and operated by a medical facility. For example, the medical care network 110 can be operated by a hospital system. In some cases, the medical care network 110 can be implemented behind a firewall. Alternatively or additionally, each of the local networks can be implemented behind a firewall.

The medical care network 110 can include one or more local networks, e.g., the local networks 130 and 140, as illustrated. Each of the local networks 130 can represent a network providing connectivity to a group of electronic devices. The group of electronic devices can be located in close proximity. In one example, the medical care network 110 can be operated by a hospital system having multiple sites in different cities, where electronic devices in each site are connected in a local network at that site. In another example, the hospital system can have multiple buildings, and can install a local network for each building or each floor of the building. In some cases, the local network can be implemented using local area network (LAN) technologies, such as wireless LAN (WLAN) or WiFi technologies, or wireless LAN technologies.

A local network, e.g., the local network 130 or 140, can provide connectivity to a plurality of electronic devices. These devices can include one or more medical equipment (ME) 136 and one or more other equipment 138. An ME 136 represents an electronic device that is specifically configured to provide medical care functions. Examples of the ME 136 include an X-ray machine, a pacemaker, a hearing aid, a dosage-pumping machine, or other medical devices that can connect to a medical care network. Other equipment 138 represents electronic devices that are not ME. For example, the other equipment 138 can include general purpose electronic devices such as endpoint, computing device, mobile device, mobile electronic device, user device, mobile station, subscriber station, portable electronic device, mobile communications device, wireless modem, wireless terminal, or the like. Examples of an endpoint may include a mobile device, cellular phone, personal data assistant (PDA), smart phone, laptop, tablet, personal computer (PC), pager, portable computer, portable gaming device, camera, vehicle, or other communications device having components for communicating voice or data. A vehicle can include a motor vehicle (e.g., automobile, car, truck, bus, motorcycle, ambulance, etc.), aircraft (e.g., airplane, unmanned aerial vehicle, unmanned aircraft system, drone, helicopter, etc.), spacecraft (e.g., spaceplane, space shuttle, space capsule, space station, satellite, etc.), watercraft (e.g., ship, boat, hovercraft, submarine, etc.), railed vehicle (e.g., train, tram, etc.), and other types of vehicles including any combinations of any of the foregoing, whether currently existing or after arising.

The MEM 134 represents an application, a set of applications, software, software modules, hardware, or any combination thereof that can be configured to monitor data transmission activities of devices connected to the local network 130. In some cases, the MEM 134 can be implemented using an electronic device that is configured to receive data packets, inspect the data packets, and transmit messages to other devices. For example, the MEM 134 can include a network interface card (NIC), a Wireless communication module, or any combinations thereof that implement communication protocols. Alternatively or additionally, the MEM 134 can be implemented as a software application on the router 132.

The MEC 120 represents an application, a set of applications, software, software modules, hardware, or any combination thereof that can be configured to control the monitoring operations of the MEM 134 and to provide input and output interfaces to an administrator for security profile provisions, device classification adjustment, and alert notifications. The MEC 120 can be implemented on-premises, e.g., in the hospital system that operates the medical care network 110. Alternatively or additionally, the MEC 120 can be implemented in a cloud computing platform. In some cases, the MEC 120 can be implemented on a distributing computing platform, which includes components in different physical locations.

In an example operation, the MEM 134 detects electronic devices such as the ME 136 and the other equipment 138 that are connected to the local network 130. The MEM 134 determines whether an electronic device is a medical equipment, such as the ME 136, or not a medical equipment, such as an other equipment 138. The MEM 134 associates a security profile with the ME 136. The MEM 134 monitors the data transmission activities of the ME 136. If the MEM 134 detects that a data transmission activity of the ME 136 violates configurations set in the security profile associated with the ME 136, the MEM 134 transmits a notification to the MEC 120 to indicate the violation. FIGS. 2-5 and associated descriptions provide additional details of these implementations.

While elements of FIG. 1 are shown as including various component parts, portions, or modules that implement the various features and functionality, nevertheless, these elements may instead include a number of sub-modules, third-party services, components, libraries, and such, as appropriate. Furthermore, the features and functionality of various components can be combined into fewer components, as appropriate.

Figure 2:
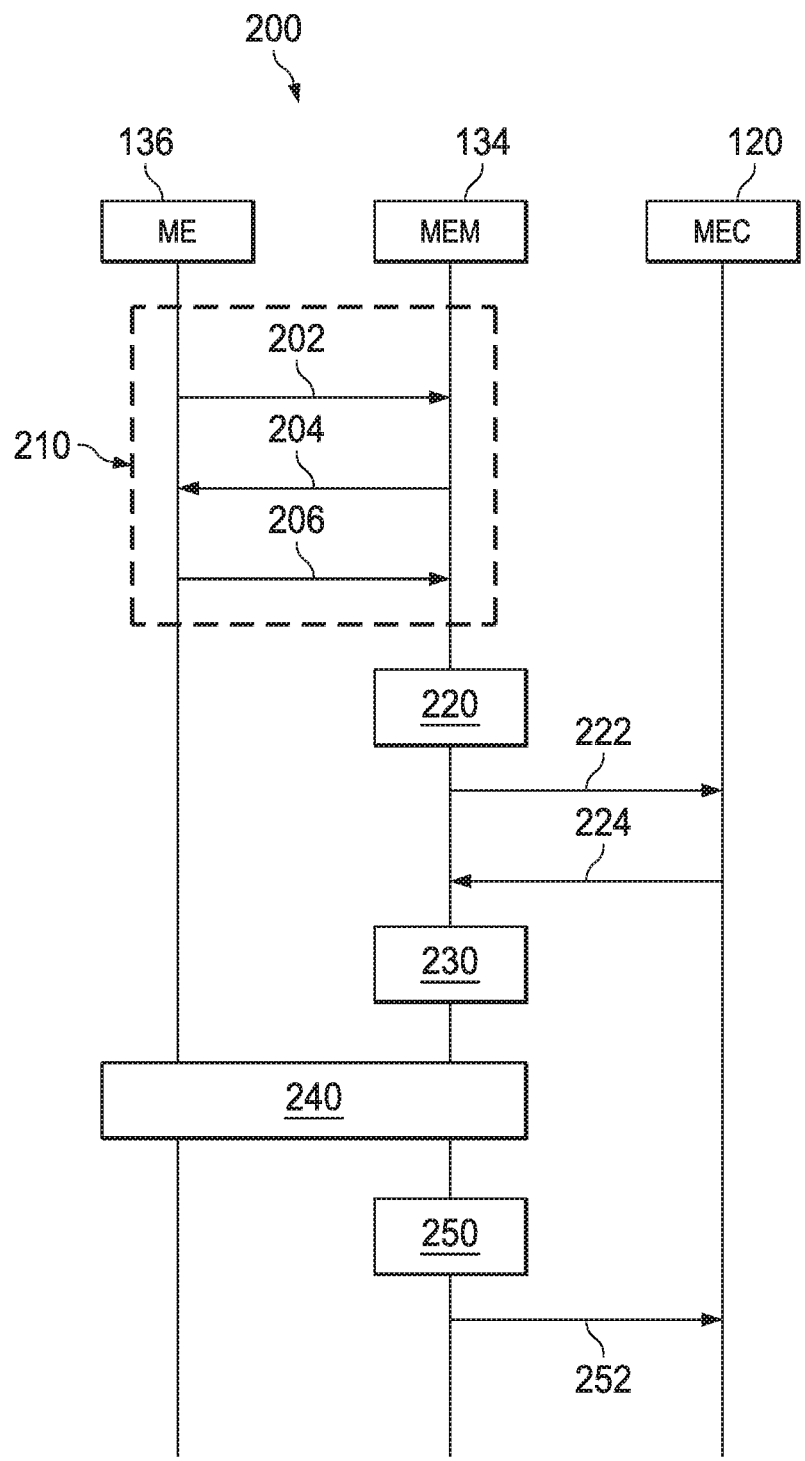
FIG. 2 is a signal flow diagram showing an example process that reduces network security risks in a medical care network, according to an implementation.

FIG. 2 is a signal flow diagram showing an example process 200 that reduces network security risks in a medical care network, according to an implementation. The process 200 can be implemented by one or more entities shown in FIG. 1, or any other systems or modules that reduce network security risks in a medical care network. For example, the process 200 can be implemented by the MEM 134, the ME 136, and the MEC 120, or a combination thereof. The example process 200, shown in FIG. 2, can also be implemented using additional, fewer, or different operations, which can be performed in the order shown or in a different order.

The example process 200 begins at 210, where the MEM 134 detects devices that are connected to the local network in which the MEM 134 is located. In some implementations, after detecting a device, the MEM 134 can assign a device identifier (ID) to the detected device. In some cases, the MEM 134 can detect the devices based on data packets that are transmitted in the local network. For example, at 202, the ME 136 transmits a data packet in the local network. The data packet can be directed to other devices in the local network, or to a device external to the local network via a router. Because the MEM 134 is located in the local network, the MEM 134 can receive the data packet. The MEM 134 can thus determine that the originating device of the data packet, e.g., the ME 136, is connected to the local network. In some implementations, the originating device of the data packet can be identified by the header of the data packet. For example, the header of the data packet can include an Internet Protocol (IP) address of the originating device, a Media Access Control (MAC) address of the originating device, a hardware identifier (ID) of the originating device, or any combinations thereof that can be used to identify the originating device. Examples of the hardware ID can include a Mobile Equipment Identifier (MEID), a Universal integrated circuit card (UICC) number, a subscriber identity module (SIM) card number.

Alternatively or in combination, the MEM 134 can detect the devices using a ping. For example, at 204, the MEM 134 can transmit a broadcast message to devices connected to the local network. The broadcast message requests the recipient to send a response. An example of the broadcast message is an Internet Control Message Protocol (ICMP) echo request. At 206, a device, e.g., the ME 136, that is connected to the local network responds to the broadcast message by transmitting a response message. An example of the broadcast message is an ICMP echo reply. The MEM 134 can identify the responding device based on metadata information of the response message. The metadata information can include information in the header of the response message, e.g., the IP address, the MAC address, the hardware ID, or the like. In some cases, the MEM 134 can perform the ping periodically. This approach enables the MEM 134 to detect devices that are not currently transmitting data.

At 220, the MEM 134 determine that the detected devices belong to one of several categories. The categories can include a monitored-device category, an unmonitored-device category, an undetermined category, or other category. The monitored-device category includes devices that are monitored by the MEM 134 to determine security risks associated with these devices. For example, the monitored-device category can include medical equipment. The unmonitored-device category includes devices that are not monitored by the MEM 134. For example, the monitored-device category can include devices that are not medical equipment. The undetermined category includes devices that are detected by the MEM 134 but cannot be classified by the MEM 134 to belong to either the monitored-device category or the unmonitored-device category. In some cases, these categories can be provisioned by the MEC 120, an administrator of the medical care network or the local network, or any combinations thereof. For example, an administrator can configure the MEM 134, either directly or using the MEC 120, to add, delete, or change types of devices that belong to any of the categories.

In some implementations, the MEM 134 can determine the category for the detected device based on the information in the header of the packet originated by the detected device. In one example, the MEM 134 can store a look up table that associates the MAC address of the packet with different equipment manufacturers. If the MAC address is found in the look up table and the corresponding equipment manufacturer is a medical equipment manufacturer, then the MEM 134 can determine that the detected device is a medical equipment, and thus belongs to the monitored-device category. In some cases, the MEM 134 can further determine the particular type of medical equipment, e.g., an X-ray machine, a pacemaker, or the like, based on the look up table. If the MAC address is found in the look up table and the corresponding equipment manufacturer is an IT device manufacturer, then the MEM 134 can determine that the detected device is not a medical equipment and thus belongs to the unmonitored-device category. In some cases, the MEM 134 can further determine the particular type of the detected device as a cellphone, a laptop, a desktop computer, or the like, based on the look up table.

In another example, the look up table can associate the types of the devices with other metadata information in the data packet, e.g., the hardware ID. Accordingly, the MEM 134 can determine the category for the detected device based on this other metadata information.

In some cases, the MEM 134 may transmit a query to the detected device. The query can be formatted according to a standardized or a proprietary protocol. For example, the query can be formatted according to an Application programming interface (API) supported by the detected device. In response, the detected device can transmit a query response, which indicates a type of the detected device. The MEM 134 can thus classify the detected device into a corresponding category.

In some implementations, the MEM 134 can perform a deep packet inspection on the data packet received from the detected device. The MEM 134 can determine the content of the data packet, and thus identify the type of the detected device. Based on the type of the detected device, the MEM 134 can classify the detected device into a corresponding category.

At 222, the MEM 134 transmits a classification report to the MEC 120. The classification report can include the IDs, the types, and any other information of detected devices in one or more categories. In some cases, the classification report can be sent periodically. Alternatively or additionally, the classification report can be triggered by an event. Example of the events include detecting a new device, classifying a new device into the undetermined category, or the like.

In some cases, the classification can be adjusted at the MEC 120. For example, the MEC 120 can output the classification report, an administrator can change the category of a device, e.g., move a device from the undetermined category to the monitored-device category or the unmonitored-device category. In some implementations, the administrator can dispatch a local support staff member to inspect a device, and report the category that the device belongs to. At 224, the MEC 120 can transmit an updated classification report to the MEM 134. The updated classification report indicates the adjustment made at the MEC 120. The MEM 134 can update the classification accordingly.

If the detected device belongs to the monitored-device category, at 230, the MEM 134 associates the detected device with a security profile. A security profile includes one or more security parameters. Each security parameter can indicate a configured network operation policy. In one example, a security parameter can indicate a connectivity restriction list. The list can be a white list, which includes the list of addresses that the detected device is authorized to communicate with, a black list, which includes the list of addresses that the detected device is not authorized to communicate with, or a combination thereof. For example, a drug-infusion pump can be configured to access a drug-dose setting controller, but not a computer storing personal information of a patient.

In another example, the security parameter can indicate a configured threshold of data packets that the detected device can transmit or receive. For example, a drug-infusion pump can be configured to transmit or receive a limited number of packets during a configured time period. In general, the number of bytes that convey dosage information is small. Therefore, if the configured threshold is reached, the drug-infusion pump may be performing unauthorized data retrieval, e.g., downloading patient records.

In another example, the security parameter can indicate a content restriction. For example, a drug-infusion pump can be configured to transmit or receive information related to dosage, but not personal information of a patient.

In some cases, the MEM 134 can store one or more security profiles. Each security profile corresponding to a particular type of medical equipment. As described previously, the MEM 134 can identify the type of the medical equipment, and associate the medical equipment with the security profile corresponding to the type of the medical equipment. In some cases, the MEM 134 can assign a default security profile to a medical equipment in case the type of the medical equipment is not identified or there is no specific security profile associated with the particular type of the medical equipment. In some cases, security profiles, including the default security profile, can be configured at the MEC 120 and transmitted to the MEM 134. The MEC 120 can also add, delete, or change the security profiles and send updates to the MEM 134.

In some implementations, security profiles can be formatted using an open data/document interchange-format, e.g., eXtensible Markup Language (XML) or JavaScript Object Notation (JSON). Following is an example security profile:

```
<CATALOG>
    <DEVICE>
        <MASTER_TYPE></MASTER_TYPE>
        <CATEGORY></CATEGORY>
        <SUBCATEGORY></SUBCATEGORY>
<NAME></NAME>
        <FDA_CLASS></FDA_CLASS>
        <FDA_PRODUCT_CODE></FDA_PRODUCT_CODE>
        <FDA_510K_NUMBER></FDA_510K_NUMBER>
<FDA_MEDICAL_SPECIALTY></FDA_MEDICAL_SPECIALTY>
        <MANUFACTURER></MANUFACTURER>
        <MAC_ADDRESS_PREFIX_LIST>
            <MAC_PREFIX></MAC_PREFIX>
<MAC_PREFIX></MAC_PREFIX>
        </MAC_ADDRESS_PREFIX_LIST>
        <CONNECTIVITY_LIST>
            <CONNECTION_TYPE></CONNECTION_TYPE>
```

-continued

```
<CONNECTION_TYPE></CONNECTION_TYPE>
</CONNECTIVITY_LIST>
    <CONNECTIVITY_TARGET_LIST>
        <TARGET></TARGET>
<TARGET></TARGET>
</CONNECTIVITY_TARGET_LIST>
    <PROTOCOL_LIST>
        <PROTOCOL></PROTOCOL>
        <PROTOCOL></PROTOCOL>
    </PROTOCOL_LIST>
    <RECORD_LIMITS>
<DAILY_PATIENT_COUNT></DAILY_PATIENT_COUNT>
    <DAILY_DATA_COUNT></DAILY_DATA_COUNT>
    </RECORD_LIMITS>
</DEVICE>
</CATALOG>
```

Table 1 lists explanations of the features described in the security profile:

TABLE 1

| Feature | Description |
| --- | --- |
| Master Type | Type of the medical device (ex. Diagnostic Imaging, Ophthalmics) |
| Category | Category of medical device |
| Sub Category | Subcategory of medical device |
| Name | Common name of the device |
| FDA Class | Class as per FDA guidelines |
| FDA Product Code | Product code as per FDA guidelines |
| FDA 510k number | Unique FDA Number |
| FDA Medical Specialty | Medical specialty of the device as per FDA guidelines |
| Manufacturer | Device Manufacturer |
| MAC Address Prefix List | List of Mac addresses prefixes associated with the device or the manufacturer. |
| Connectivity List | List of connection types made or received by the device |
| Connectivity Target List | List of resources and resource types that the device is expected to connect to |
| Protocol List | List of protocols that are to be used by the device |
| Record Limits | Expected amount of data transferred to the device in different variable types, such as amount of data per day and number of patient records read. |

At 240, the MEM 134 monitors the network activity of the detected device, e.g., the ME 136. In some cases, the MEM 134 monitors the network activity by inspecting the data packets that are transmitted from the ME 136 or to the ME 136. For example, the MEM 134 can inspect the header of the data packet. The MEM 134 can identify the originating device and the target device of the data packet based on the source and target addresses in the header. The MEM 134 can determine whether the originating device or the target device belong to a device in the monitored-device category. If neither the originating device nor the target device belongs to a device in the monitored-device category, the MEM 134 can discard the data packet without further inspection.

If the originating device, the target device, or both belong to a device in the monitored-device category, for example, the originating device is determined to the ME 136, at 250, the MEM 134 can determine whether the transmission of the data packet is in conflict with one or more security parameters configured in the security profile associated with the ME 136. In one example, the MEM 134 can determine whether the data packet is transmitted to an address that is in conflict with the connectivity restriction list configured in the security profile associated with the ME 136. In another example, the MEM 134 can also determine that the size of the data packet, or the accumulated data size transmitted by the ME 136, is in conflict with the configured data threshold in the security profile associated with the ME 136. In yet another example, the MEM 134 can further inspect the content of the data packet, and determine that the data packet violates the content restriction configured in the security profile associated with the ME 136. In some implementations, the MEM 134 can log a transmission event associated with the data packet. The MEM 134 can use the log to determine if the accumulated data activity of the ME 136 violates a security parameter configured in the security profile.

In response to detecting a conflict with the security parameter in the security profile associated with the ME 136, at 252, the MEM 134 transmits a notification to the MEC 120. The notification can include the device ID of the ME 136, the information of the data packet, including, for example, the source and target addresses or the size, the security parameter that is violated, or other additional information. In some cases, the MEM 134 can output an alert, e.g., an audio or visual alert. The MEM 134 can also transmit the alert to another device, e.g., in a short message service (SMS) message or an email to a mobile device carried by an administrator. The administrator can review the alert and perform corresponding security measures. For example, the administrator can dispatch a support staff to inspect the ME 136 can determine whether the ME 136 is affected by security breaches and should be taken offline.

Figure 3:
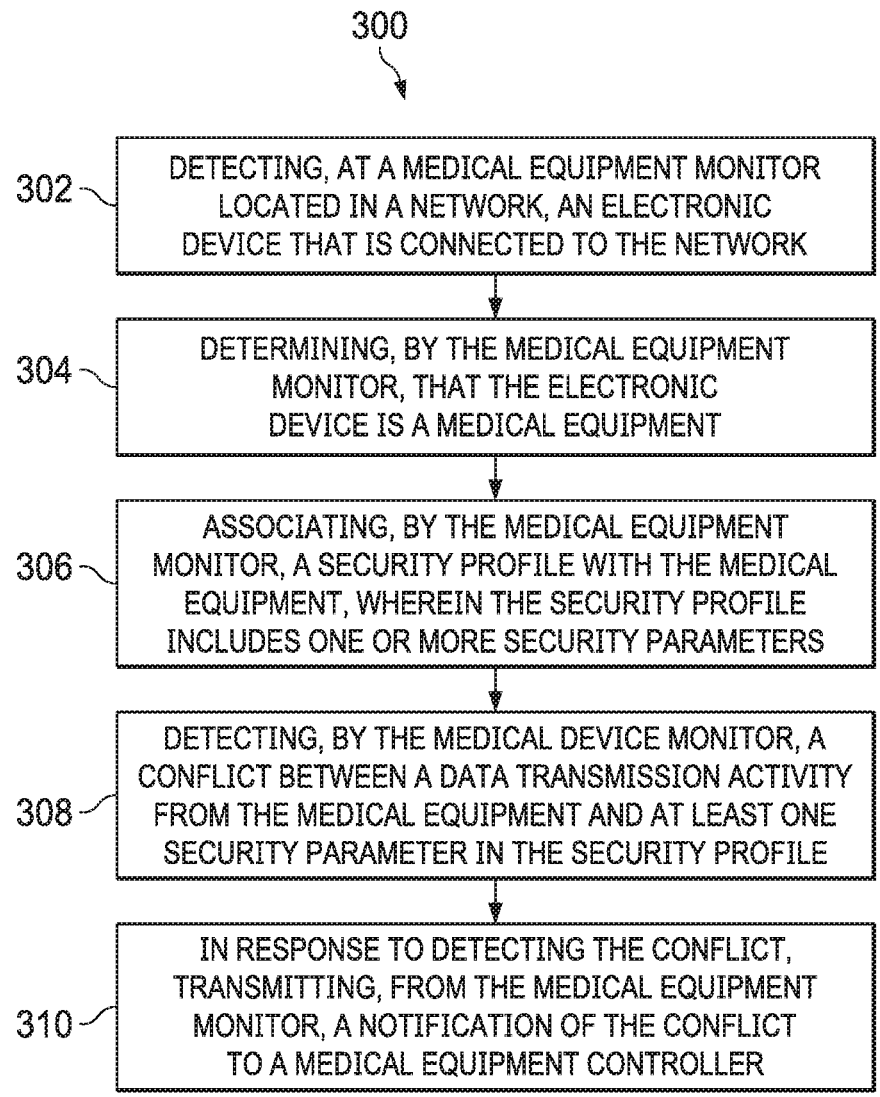
FIG. 3 is a flow diagram showing an example method that reduces network security risks in a medical care network.

FIG. 3 is a flow diagram showing an example method 300 that reduces network security risks in a medical care network, according to an implementation. The method 300 can be implemented by an MEM, e.g., the MEM 134 shown in FIGS. 1 and 2. The method 300 shown can also be implemented using additional, fewer, or different entities. Furthermore, the method 300 can be implemented using additional, fewer, or different operations, which can be performed in the order shown or in a different order.

The example method 300 begins at 302, where an MEM located in a network detects an electronic device that is connected to the network. At 304, the MEM determines that the electronic device is a medical equipment. At 306, the MEM associates a security profile with the medical equipment. The security profile includes one or more security parameters. At 308, the MEM detects a conflict between a data transmission activity from the medical equipment and at least one security parameter in the security profile. At 310, in response to detecting the conflict, the MEM transmits a notification of the conflict to a medical equipment controller.

Figure 4:
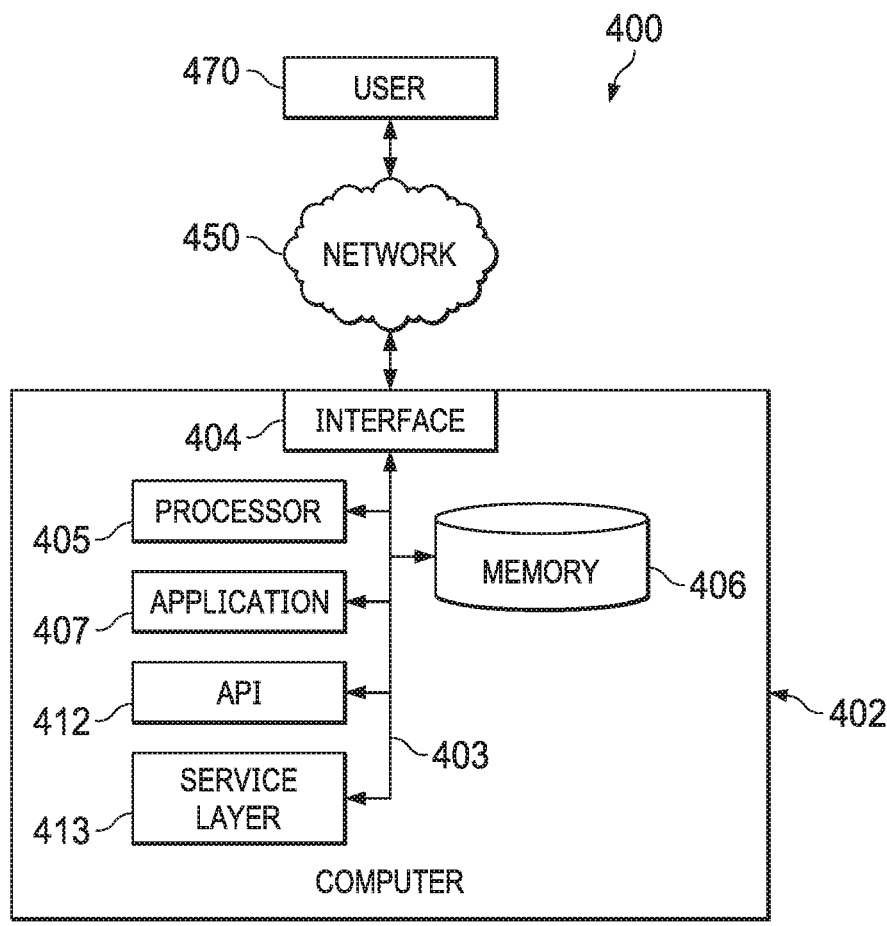
FIG. 4 is a high-level architecture block diagram of a computing system, according to an implementation.

FIG. 4 is a high-level architecture block diagram of a computing system 400, according to an implementation. At a high level, the illustrated system 400 includes a computer 402 that is communicably coupled with a network 450. The described illustration is only one possible implementation of the described subject matter and is not intended to limit the disclosure to the single described implementation. Those of ordinary skill in the art will appreciate the fact that the described components can be connected, combined, or used in alternative ways consistent with this disclosure.

The network 450 facilitates communications between the components of the system 400. In some cases, a user 470 can access the computer 402 from a remote network. In these or other cases, the network 450 can be a wireless or a wireline network. In some cases, the user 470 can access the computer 402 locally. In these or other cases, the network 450 can also be a memory pipe, a hardware connection, or any internal or external communication paths between the components. The user 470 can be an administrator of a medical care network.

The computer 402 includes a computing system configured to perform the algorithm described in this disclosure. For example, the computer 402 can be used to implement an MEC. In some cases, the algorithm can be implemented in an executable computing code, e.g., C/C++ executable codes. Alternatively or in combination, the algorithm can be implemented in an application program, e.g., EXCEL. In some cases, the computer 402 can include a standalone Linux system that runs batch applications. In some cases, the computer 402 can include mobile or personal computers that run the application program.

The computer 402 may include an input device, such as a keypad, keyboard, touch screen, microphone, speech recognition device, other device that can accept user information, and/or an output device that conveys information associated with the operation of the computer 402, including digital data, visual and/or audio information, or a GUI.

The computer 402 can serve as a client, network component, a server, a database or other persistency, and/or any other component of the system 400. In some implementations, one or more components of the computer 402 may be configured to operate within a cloud-computing-based environment.

At a high level, the computer 402 is an electronic computing device operable to receive, transmit, process, store, or manage data and information associated with the system 400. According to some implementations, the computer 402 may also include, or be communicably coupled with, an application server, e-mail server, web server, caching server, streaming data server, business intelligence (BI) server, and/or other server.

The computer 402 can receive requests over network 450 from a client application (e.g., executing on another computer 402) and respond to the received requests by processing the said requests in an appropriate software application. In addition, requests may also be sent to the computer 402 from internal users (e.g., from a command console or by another appropriate access method), external or third parties, other automated applications, as well as any other appropriate entities, individuals, systems, or computers.

Each of the components of the computer 402 can communicate using a system bus 403. In some implementations, any and/or all the components of the computer 402, both hardware and/or software, may interface with each other and/or the interface 404 over the system bus 403, using an application programming interface (API) 412 and/or a service layer 413. The API 412 may include specifications for routines, data structures, and object classes. The API 412 may be either computer language-independent or -dependent and refer to a complete interface, a single function, or even a set of APIs. The service layer 413 provides software services to the computer 402 and/or the system 400. The functionality of the computer 402 may be accessible for all service consumers using this service layer. Software services, such as those provided by the service layer 413, provide reusable, defined business functionalities through a defined interface. For example, the interface may be software written in JAVA, C++, or other suitable language providing data in Extensible Markup Language (XML) format or other suitable format. While illustrated as an integrated component of the computer 402, alternative implementations may illustrate the API 412 and/or the service layer 413 as stand-alone components in relation to other components of the computer 402. Moreover, any or all parts of the API 412 and/or the service layer 413 may be implemented as child or sub-modules of another software module, enterprise application, or hardware module without departing from the scope of this disclosure.

The computer 402 includes an interface 404. Although illustrated as a single interface 404 in FIG. 4, two or more interfaces 404 may be used according to particular needs, configurations, or particular implementations of the computer 402. The interface 404 is used by the computer 402 for communicating with other systems in a distributed environment—including within the system 400—connected to the network 450—(whether illustrated or not). Generally, the interface 404 comprises logic encoded in software and/or hardware in a suitable combination and operable to communicate with the network 450. More specifically, the interface 404 may comprise software supporting one or more communication protocols associated with communications such that the network 450 or interface's hardware is operable to communicate physical signals within and outside of the illustrated system 400.

The computer 402 includes a processor 405. Although illustrated as a single processor 405 in FIG. 4, two or more processors may be used according to particular needs, configurations, or particular implementations of the computer 402. Generally, the processor 405 executes instructions and manipulates data to perform the operations of the computer 402. In some cases, the processor 405 can include a data processing apparatus.

The computer 402 also includes a memory 406 that holds data for the computer 402. Although illustrated as a single memory 406 in FIG. 4, two or more memories may be used according to particular needs, configurations, or particular implementations of the computer 402. While memory 406 is illustrated as an integral component of the computer 402, in alternative implementations, memory 406 can be external to the computer 402.

The application 407 is an algorithmic software engine providing functionality according to particular needs, configurations, or particular implementations of the computer 402, particularly with respect to functionality required for performing the algorithm described herein. Although illustrated as a single application 407, the application 407 may be implemented as multiple applications 407 on the computer 402. In addition, although illustrated as integral to the computer 402, in alternative implementations, the application 407 can be external to the computer 402.

There may be any number of computers 402 associated with, or external to, the system 400 and communicating over network 450. Further, the terms "client," "user," and other appropriate terminology may be used interchangeably, as appropriate, without departing from the scope of this disclosure. Moreover, this disclosure contemplates that many users may use one computer 402, or that one user may use multiple computers 402.

Figure 5:
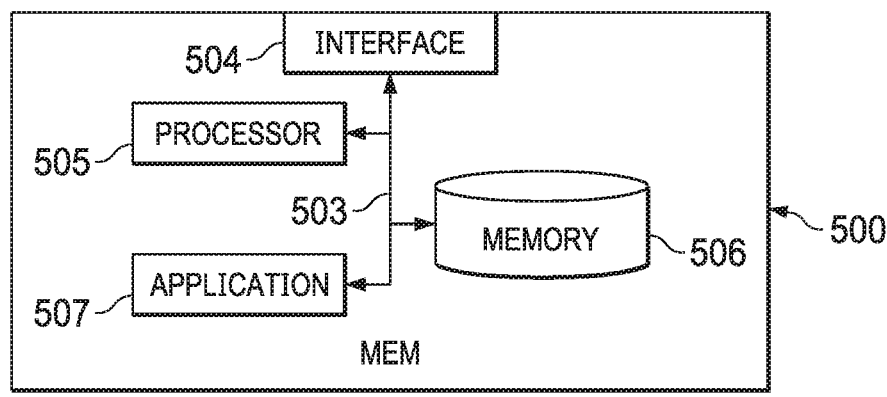
FIG. 5 is a high-level architecture block diagram of a medical equipment monitor, according to an implementation.

FIG. 5 is a high-level architecture block diagram of a MEM 500, according to an implementation. The described illustration is only one possible implementation of the described subject matter and is not intended to limit the disclosure to the single described implementation. Those of ordinary skill in the art will appreciate the fact that the described components can be connected, combined, or used in alternative ways consistent with this disclosure.

At a high level, the MEM 500 is an electronic computing device operable to receive, transmit, process, store, or manage data and information according to the described subject matter in the disclosure. The MEM 500 can receive and transmit data packets over a network that is connected with the MEM 500. Each of the components of the MEM 500 can communicate using a system bus 503.

The MEM 500 includes an interface 504. Although illustrated as a single interface 504 in FIG. 5, two or more interfaces 504 may be used according to particular needs, configurations, or particular implementations of the MEM 500. The interface 504 is used by the MEM 500 for communicating with other systems in a distributed environment. Generally, the interface 504 comprises logic encoded in software and/or hardware in a suitable combination and operable to communicate with a network. More specifically, the interface 504 may comprise software supporting one or more communication protocols associated with communications such that the network or interface's hardware is operable to communicate physical signals other devices connected to the interface 504.

The MEM 500 includes a processor 505. Although illustrated as a single processor 505 in FIG. 5, two or more processors may be used according to particular needs, configurations, or particular implementations of the MEM 500. Generally, the processor 505 executes instructions and manipulates data to perform the operations of the MEM 500. In some cases, the processor 505 can include a data processing apparatus.

The MEM 500 also includes a memory 506 that holds data for the MEM 500. Although illustrated as a single memory 506 in FIG. 5, two or more memories may be used according to particular needs, configurations, or particular implementations of the MEM 500. While memory 506 is illustrated as an integral component of the MEM 500, in alternative implementations, memory 506 can be external to the MEM 500.

The application 507 is an algorithmic software engine providing functionality according to particular needs, configurations, or particular implementations of the MEM 500, particularly with respect to functionality required for performing the algorithm described herein. Although illustrated as a single application 507, the application 507 may be implemented as multiple applications 507 on the MEM 500. In addition, although illustrated as integral to the MEM 500, in alternative implementations, the application 507 can be external to the MEM 500.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, e.g., a central processing unit (CPU), an FPGA (field programmable gate array), or an ASIC (application specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, an FPGA, or an ASIC.

Computers suitable for the execution of a computer program can be based on general or special purpose microprocessors, both, or any other kind of CPU. Generally, a CPU will receive instructions and data from a read only memory (ROM) or a random access memory (RAM), or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer readable media, transitory or non-transitory, suitable for storing computer program instructions and data include all forms of non-volatile memory, media and memory devices, including by way of example, semiconductor memory devices, e.g., erasable programmable read-only memory (EPROM), electrically erasable programmable read-only memory (EEPROM), and flash memory devices; magnetic disks, e.g., internal hard disks or removable disks; magneto optical disks; and CD ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to, or represent, the functions of the web browser.

While this disclosure contains many specific implementation details, these should not be construed as limitations on the scope of any invention or on the scope of what may be claimed, but rather as descriptions of features that may be specific to particular implementations of particular inventions. Certain features that are described in this disclosure in the context of separate implementations can also be implemented, in combination, in a single implementation. Conversely, various features that are described in the context of a single implementation can also be implemented in multiple implementations, separately or in any suitable sub-combination. Moreover, although features may be described above as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the implementations described above should not be understood as requiring such separation or integration in all implementations, and it should be understood that the described program components and systems can generally be integrated together in a single software product or packaged into multiple software products.

Accordingly, the above description of example implementations does not define or constrain this disclosure. Other changes, substitutions, and alterations are also possible without departing from the spirit and scope of this disclosure.

Furthermore, any claimed implementation below is considered to be applicable to at least a computer-implemented method; a transitory or non-transitory, computer-readable medium storing computer-readable instructions to perform the computer-implemented method; and a computer system comprising a computer memory interoperably coupled with a hardware processor configured to perform the computer-implemented method or the instructions stored on the computer-readable medium.

What is claimed is:

1. A method for reducing network security risk in medical devices, comprising:
   detecting, at a medical equipment monitor located in a network, an electronic device that is connected to the network;
   determining, by the medical equipment monitor, that the electronic device comprises medical equipment based on a data packet that is transmitted by the electronic device over the network, wherein the determining comprises:
      identifying a media access control (MAC) address in a header of the data packet; and
      determining that the electronic device comprises the medical equipment based on the MAC address and a lookup table that associates MAC addresses with medical equipment manufacturers;
   associating, by the medical equipment monitor, a network security profile with the medical equipment, wherein the network security profile includes one or more security parameters of network data transmission activity, and wherein associating the network security profile with the medical equipment comprises:

identifying a type of the medical equipment;
searching stored network security profiles, wherein the stored network security profiles include a default network security profile; and
selecting the network security profile among the stored network security profiles based on the type of the medical equipment, wherein different types of medical equipment correspond to different security parameters of network data transmission activity in the respective network security profile, the security parameters include a threshold of accumulated data size transmitted by the medical equipment and a permitted type of content information with the type of medical equipment, and the selecting comprises:
matching the type of the medical equipment with types of medical equipment that correspond to the stored network security profiles;
selecting the default network security profile when the type of the medical equipment does not match any type of medical equipment corresponding to other stored network security profiles, and
wherein the selected network security profile includes a connectivity restriction list, and the connectivity restriction list includes one or more addresses in the network that are allowed to transmit data packets to or receive data packets from the type of the medical equipment;
detecting, by the medical equipment monitor, a conflict between a data transmission activity from the medical equipment and at least one security parameter in the network security profile, wherein the detecting the conflict comprises detecting that the medical equipment transmits a data packet to an address not included in the connectivity restriction list; and
in response to detecting the conflict, transmitting, from the medical equipment monitor, a notification of the conflict to a medical equipment controller.

2. The method of claim 1, wherein the data packet is received in response to an Internet Control Message Protocol (ICMP) ping transmitted by the medical equipment monitor.

3. The method of claim 1, wherein the at least one security parameter comprises a connectivity restriction list, and detecting the conflict comprises detecting that the data transmission activity is directed to at least one address on the connectivity restriction list.

4. The method of claim 1, wherein the at least one security parameter indicates a content restriction, and detecting the conflict comprises detecting that the data transmission activity violates the content restriction.

5. A medical equipment monitor, wherein the medical equipment monitor comprises:
at least one hardware processor; and
a non-transitory computer-readable storage medium coupled to the at least one hardware processor and storing programming instructions for execution by the at least one hardware processor, wherein the programming instructions, when executed, cause the at least one hardware processor to perform operations for reducing network security risk in medical devices, wherein the operations comprise:
detecting, at the medical equipment monitor located in a network, an electronic device that is connected to the network;
determining, by the medical equipment monitor, that the electronic device comprises a medical equipment based on a data packet that is transmitted by the electronic device over the network, wherein the determining comprises:
identifying a media access control (MAC) address in a header of the data packet; and
determining that the electronic device comprises the medical equipment based on the MAC address and a lookup table that associates MAC addresses with medical equipment manufacturers;
associating, by the medical equipment monitor, a network security profile with the medical equipment, wherein the network security profile includes one or more security parameters of network data transmission activity, and wherein associating the network security profile with the medical equipment comprises:
identifying a type of the medical equipment;
searching stored network security profiles, wherein the stored network security profiles include a default network security profile; and
selecting the network security profile among the stored network security profiles based on the type of the medical equipment, wherein different types of medical equipment correspond to different security parameters of network data transmission activity in the respective network security profile, the security parameters include a threshold of accumulated data size transmitted by the medical equipment and a permitted type of content information with the type of medical equipment, and the selecting comprises:
matching the type of the medical equipment with types of medical equipment that correspond to the stored network security profiles;
selecting the default network security profile when the type of the medical equipment does not match any type of medical equipment corresponding to other stored network security profiles, and
wherein the selected network security profile includes a connectivity restriction list, and the connectivity restriction list includes one or more addresses in the network that are allowed to transmit data packets to or receive data packets from the type of the medical equipment;
detecting, by the medical equipment monitor, a conflict between a data transmission activity from the medical equipment and at least one security parameter in the network security profile, wherein the detecting the conflict comprises detecting that the medical equipment transmits a data packet to an address not included in the connectivity restriction list; and
in response to detecting the conflict, transmitting, from the medical equipment monitor, a notification of the conflict to a medical equipment controller.

6. The medical equipment monitor of claim 5, wherein the data packet is received in response to an Internet Control Message Protocol (ICMP) ping transmitted by the medical equipment monitor.

7. The medical equipment monitor of claim 5, wherein the at least one security parameter indicates a content restriction, and detecting the conflict comprises detecting that the data transmission activity violates the content restriction.

8. One or more non-transitory computer-readable media containing instructions which, when executed, cause a computing device to perform operations for reducing network security risk in medical devices, wherein the operations comprise:

detecting, at a medical equipment monitor located in a network, an electronic device that is connected to the network;

determining, by the medical equipment monitor, that the electronic device comprises a medical equipment based on a data packet that is transmitted by the electronic device over the network, wherein the determining comprises:

identifying a media access control (MAC) address in a header of the data packet; and determining that the electronic device comprises the medical equipment based on the MAC address and a lookup table that associates MAC addresses with medical equipment manufacturers;

associating, by the medical equipment monitor, a network security profile with the medical equipment, wherein the network security profile includes one or more security parameters of network data transmission activity, and wherein associating the network security profile with the medical equipment comprises:

identifying a type of the medical equipment;

searching stored network security profiles, wherein the stored network security profiles include a default network security profile; and selecting the network security profile based on the type of the medical equipment, wherein different types of medical equipment correspond to different security parameters of network data transmission activity in the respective network security profile, the security parameters include a threshold of accumulated data size transmitted by the medical equipment and a permitted type of content information with the type of medical equipment, and the selecting comprises:

matching the type of the medical equipment with types of medical equipment that correspond to the stored network security profiles;

selecting the default network security profile when the type of the medical equipment does not match any type of medical equipment corresponding to other stored network security profiles, and wherein the selected network security profile includes a connectivity restriction list, and the connectivity restriction list includes one or more addresses in the network that are allowed to transmit data packets to or receive data packets from the type of the medical equipment;

detecting, by the medical equipment monitor, a conflict between a data transmission activity from the medical equipment and at least one security parameter in the network security profile, wherein the detecting the conflict comprises detecting that the medical equipment transmits a data packet to an address not included in the connectivity restriction list; and in response to detecting the conflict, transmitting, from the medical equipment monitor, a notification of the conflict to a medical equipment controller.

9. The one or more computer-readable media of claim 8, wherein the data packet is received in response to an Internet Control Message Protocol (ICMP) ping transmitted by the medical equipment monitor.

\* \* \* \* \*